United States Patent [19]
Wöber et al.

[11] Patent Number: 6,124,110
[45] Date of Patent: Sep. 26, 2000

[54] METHOD FOR DETERMINING ACTIVATED COAGULATION FACTORS IN PLASMA AND PLASMA DERIVATIVES

[75] Inventors: Guenter Wöber, Hagen; Beate Gesien, Wetter, both of Germany

[73] Assignee: DRK-Blutspendedienst Nordrheinwestfalen gGmbH, Hagen, Germany

[21] Appl. No.: 09/402,332

[22] PCT Filed: Mar. 6, 1998

[86] PCT No.: PCT/EP98/01264

§ 371 Date: Dec. 13, 1999

§ 102(e) Date: Dec. 13, 1999

[87] PCT Pub. No.: WO98/45713

PCT Pub. Date: Oct. 15, 1998

[30] Foreign Application Priority Data

Apr. 9, 1997 [DE] Germany ............... 197 14 599

[51] Int. Cl.$^7$ ............... C12Q 1/00; C12Q 1/56
[52] U.S. Cl. ............... 435/13; 435/4
[58] Field of Search ............... 435/13, 4

[56] References Cited

U.S. PATENT DOCUMENTS

| | | |
|---|---|---|
| 5,059,525 | 10/1991 | Bartl et al. ............... 435/13 |
| 5,472,850 | 12/1995 | Morrissey ............... 435/13 |
| 5,677,162 | 10/1997 | Zou et al. ............... 435/13 |
| 5,972,681 | 10/1999 | Morita ............... 435/13 |

*Primary Examiner*—Louise N. Leary
*Attorney, Agent, or Firm*—Milde, Hoffberg & Macklin, LLP

[57] ABSTRACT

The invention relates to a method for determining activated coagulation factors in plasma or plasma derivatives. A sample of the plasma or plasma derivative to be examined is incubated with an activated prothrombin complex and pro-coagulative phospholipid vesicles, the latter containing integrated tissue factor, and thrombin formation is initiated by addition of an appropriate amount of Ca ions. After a determined incubation time, thrombin formation is terminated and the amount of thrombin formed is determined by known methods.

7 Claims, No Drawings

METHOD FOR DETERMINING ACTIVATED COAGULATION FACTORS IN PLASMA AND PLASMA DERIVATIVES

BACKGROUND OF THE INVENTION

The present invention relates to a method to determine activated blood clotting factors in plasma and plasma derivatives.

When plasma is stored at low temperatures or in the course of purification processes, activated blood clotting factors can occur in the plasma or in plasma derivatives. Generally, blood clotting factors are enzymatically inactive proenzymes that are converted into their biologically active form through limited proteolytic splitting. Thus, at the end of the clotting cascade thrombin (activated factor II–factor IIa), which splits fibrinogen, results from prothrombin (factor II), for example. In addition, thrombin activates factor XIII, which bonds fibrin to a stable coagulate. In most cases, this physiological activation is desired.

Not desired, however, is an artificial activation of blood clotting factors in stored plasma or in the production of a purified prothrombin complex of plasma, containing factors II, VII, IX, X as therapeutically effective components. When treating patients with severe coagulation deficiencies with prothrombin complex concentrates, e.g., through blood loss at serious operations, thrombo-haemorrhagic complications, whose cause is unknown, may occur as undesired side effects. It is certain, however, that the risk of such complications is increased through tissue thromboplastin, which circulates in a pathologically high concentration in the circulatory system of a patient after a severe operation. It is also suspected that activated factors IX or X in prothrombin complex concentrates contribute to an increased thromboses risk.

For this reason, laboratory tests are performed on the mentioned plasmas and plasma derivatives to verify the absence of activated factors. For plasma, a method is known for selective measurement of factor VIIa in the presence of factor VII (U.S. Pat. No. 5,472,850). In the patent publication, an assay for factor VIIa is described which uses a truncated (shortened) tissue factor tTF. The tissue factor is an integral membrane protein that binds both factor VII and factor VIIa with great affinity and in doing so initiates the clotting cascade. In addition, the complex consisting of factor VIIa and tissue factor catalyzes the activation of factor VII to factor VIIa. The patent describes a mutant form of the tissue factor, whose amino acid sequence is truncated by the portion of the protein that is responsible for the bonding to the membrane. The now soluble tissue factor tTF can bind factor VIIa and is fully active in a coagulation test. However, it lost its capability for auto-catalysis of factor VII to factor VIIa. Thus, with the use of such a soluble mutant tissue factor in a coagulation test, it is possible to determine selective factor VIIa in the presence of factor VII in plasma. However, the test is relatively complicated to carry out and offers only a result stating the presence of factor VIIa.

With prothrombin complex PPSB, a coagulation test is known and described under the designation NAPPT (non-activated partial prothrombin time) is stipulated as standard test (cf. H. S. KINGDON et al.; "Potentially Thrombogenic Materials in Factor IX Concentrates"; *Thromb. Diath. Haemorrh.* 1975; pp. 617–631).

In this test, the clotting time of plasma is measured in the presence of the sample to be analyzed in the absence of substances such as kaolin that initiate coagulation in vitro. In the absence of activating factors, the clotting time is about 150 sec; in the presence of activating factors, the clotting time is shortened. However, this test is not very sensitive and does not indicate activating factors in all instances. A critique of this test can be found in the article by C. V. PROWSE and A. E. WILLIAMS; "A Comparison of the in vitro and in vivo Thrombogenic Activity ... "; *Thromb. Haemost.* 1980, pp. 81–86.

SUMMARY OF THE INVENTION

This poses the task, and the present invention has the objective, of presenting a more precise and more sensitive test to determine the presence of activating factors where said test presents a broad spectrum of activating factors.

This objective is achieved by a method with the following process steps:

a) A sample amount of plasma or plasma derivative is incubated with activated prothrombin complex and procoagulating phospholipid vesicles, the latter containing integrated tissue factor, and the thrombin generation is initiated by adding a suitable amount of Ca ions.

b) After a specified incubation time of, for example, 5 min and 10 min, the thrombin generation is ended and the amount of generated thrombin is measured using known methods.

Known is a test method (Y. SULTAN, F. LOYER, "In Vitro Evaluation of Factor VIII-bypassing Activity ... "; *J. Lab. Clin, Med.* 1993, p. 444 pp.) where a thrombin generation is induced in the presence of a blood platelet suspension activated with collagen. Prior to each test formulation, blood platelets must be prepared from whole blood by repeated centrifugation, washed and set to a specific cell number. Such platelet suspensions are only stable for a few hours and cannot be preserved. This results in a costly activity that can only be carried out by practiced operators, which limits the application of this known test to highly qualified and best-equipped laboratories.

The new test method, on the other hand, works with materials that can be produced in practically unlimited amounts and that can be stored for a long time such that tests can be performed without the delay due to formulating a blood platelet suspension.

The new test measures the thrombin generation in defibrinated plasma in the presence of activated factors. The amount of generated thrombin is measured by applying known methods through splitting a synthetic substrate, for example the known S 2238 (cf. H. P. Shwarz et al.; *Kyoto Satellite Symposia of XIIth Congress of ISTH*; Kyoto, Japan, 1989; p 34–Abstract). The resultant coloration is measured photometrically.

Aside from defibrinated plasma, a test formulation also contains a small amount of an activated prothrombin complex and procoagulating phospholipid vesicles; with the latter containing integrated tissue factors. The reason for selecting the presence of activated prothrombin complex is that due to the auto-catalytic nature of the thrombin generation with very small amounts of activated factors, the lag phase of the thrombin generation would differ in length.

It would be impossible to specify after which incubation times to measure the thrombin generation. If, however, a "base noise level" is set through adding a small, specified amount of activated prothrombin complex, this "noise level" is amplified by the activated factors. In this case, one can always measure after the same incubation times, for example after 5 and 10 minutes. It should be emphasized that especially the use of the minimally "activated" prothrombin complex in this test and the ability to determine activated factors XII, XI, IX and VII in one test establish the particular value of the invention.

It has proven advantageous if the content of factor Xa in activated prothrombin complex is about 1% of the total factor X content with a non-measurable content of factor IIa because this leads to the best reproducible "base noise level".

The tissue factor to be used is produced from biogenic starting material, where particularly dry acetone powder is extracted from bovine brain with a detergent-containing solution.

For integration in procoagulating phospholipid vesicles in detergent-containing solution, the tissue factor is mixed with phosphatidylserine and phosphatidylcholine and integrated in the procoagulating phospholipid vesicles by dialysis.

DESCRIPTION OF THE PREFERRED EMBODIMENTS

Exemplary embodiments of the invention are explained in connection with the following examples:

Example 1:

1. Production of Defibrinated Plasma

Ancrod (the poison of the snake species Ankistrodon rhodostoma; Sigma Chemical C.: Art. No. A 5042) is diluted to 10 U/ml using distilled water. 1 ml of human plasma from normal donors is mixed with 10 μl of Ancrod solution, incubated for 1 hour at 37° C., quickly chilled to −70° C., reheated to 37° C. and centrifuged. The supernatant, defibrinated plasma, is stored at room temperature and must be used within 10 minutes. The defibrinated plasma can also be portioned and frozen. It contains only negligible traces if thrombin.

2. Production of the Partial Prothrombin Complex (PPC)

Required Reagents:

standard plasma

DEAE-Sephadex A 50 elution solution: 30 g NaCl per liter of distilled water wash buffer. 9 g $Na_2HPO_4.2$ $H_2O+7$ g NaCl per liter distilled water, pH adjusted to 7.0;

equilibration buffer. 6 g $Na_3$-citrate.2 $H_2O+7$ g NaCl per liter distilled water, pH not adjusted.

50 ml normal plasma is frozen, defrosted overnight at 4° C. and centrifuged for 15 min. The supernatant is "cryogenic supernatant"; 0.5 units of heparin are added per ml cryogenic supernatant to the latter.

DEAE-Sephadex is swelled for 15 minutes in 1 M NaCl solution at room temperature (21–24° C.) or overnight at 4° C. (20 mg dry mass to 2 ml solution), re-suspended by repeated filtration through a nylon net and equilibrated in an equilibration buffer. Heparin-binding proteins are absorbed from the cryogenic supernatant to the ion exchanger by incubation at 4° C. for one hour. In this manner 40 ml cryogenic supernatant is added to equilibrated DEAE-Sephadex corresponding to 20 mg dry mass. The loaded DEAE-Sephadex is filtered and purified in wash buffer through re-suspending. After renewed filtering, the DEAE-Sephadex is suspended in 1 ml of elution buffer and shaken at room temperature for 15 minutes.

After removing the DEAE-Sepahdex, the solution of the partial prothrombin complex is dialyzed over night against distilled water pre-cooled to 4° C. and frozen in portions. 3. Production of the Activated Prothrombin Complex (APC)

A suitable dilution of the PPC according to point 2 must be detected in the thrombin generation test (see point 5). For this purpose, a dilution series is made using HEPES buffer (e.g., 1:20, 1:40 and 1:80; HEPES=N-(2hydroxyethyl) piperazin-N'-(2-ethane sulphonic acid). Each dilution is incubated for 5 minutes at 37° C. with $CaCl_2$ in a final concentration of 10 mM. A suitable dilution is characterized by the linearity of the speed of splitting of the chromogenic substrate S 2238. The ready-to-use APC can be frozen in portions. Using this procedure, a reproducible APC can be produced with a factor Xa content of about 1% of the total factor X in the preparation. After incubation of the APC, thrombin is not detectable with the chromogenic substrate S 2238.

4. Manufacture of Procoagulating Phospholipid Vesicles With Integrated Tissue Factor Required Reagents:

dialysis hose, cellulose membrane of Sigma (item no. D 9402) or Slide-A-Lyzer™ dialysis cassette from Pierce;

dry acetone powder from bovine brain (Brain Acetone Powder, Sigma, item no. B 0508);

n-octyl-β-D-glucopyranoside (short, octyl glucoside) from Alexis (item no. 500-001-G005); 100 mg/ml distilled water (10% G/V solution);

phosphatidylserine (PS), (Sigma, item no. P 1185)

phosphatidylcholine (PC), (Sigma, item no. P 4139). Both phospholipids may contain unsaturated but preferably saturated fatty acids;

dialysis buffer in the form of 94.5 g saccharose and 0.27 g NaCl per liter of distilled water. The dialysis buffer may also contain 0.5% $NaN_3$. 0.216 g dry acetone powder is digested with 1 ml of 10% octylglucoside solution at about 30° C. in an ultrasound bath under shaking. The insoluble portion is removed by centrifuging; per ml of supernatant, 20 mg phospholipid solution (mole ratio PC to PS 6 to 4) is dissolved and dialyzed against the dialysis buffer. With daily change of the dialysis buffer, dialysis is carried out for 3 days, then two more days against a dialysis buffer that contains a gel for binding detergents (e.g., Biorad SM-2). The detergent is removed through dialysis, and a suspension of vesicles is generated spontaneously that contains the tissue factor in an integrated manner. The obtained vesicles can be frozen in portions.

With each new preparation, a suitable dilution is searched for using the blind value in the thrombin generation test (see point 5), where the blind value shall be a delta OD of 0.005 to 0.010.

5. Thrombin Generation Test

Required Reagents:

HEPES/NaCl buffer. 6 mM HEPES, 139 mM NaCl, 3.5 g albumin per 1 buffer, pH 7.35;

citrate buffer: 20 mM $Na_3$-citrate.2 $H_2O$, 125 mM NaCl, pH 7.35;

starting solution 375 mM $CaCl_2$, stop solution 40 mM EDTA;

APC and vesicle (point 4) with integrated tissue factor in a suitable dilution 5.1 Test of the plasma for a presence of activated clotting factors In a known manner 1% Triton X-100 and 1% Tributyl phosphate is added to pooled plasma made either of whole blood or through plasmaphoresis to inactivate membrane-sheathed viruses (Neurath, A. R. and Horowitz, B., EP-PS 131 740) and incubated for 4 hours at 30° C.). Thereafter, the two chemicals are removed in a known manner through hydrophobic chromatography (Bonomo, R. J., EP-PS 366 946). To prepare for the test for present activated clotting factors, a plasma sample is difibrinated as described in example 1.

Pipetting Scheme
  for the blind value: 250 µl HEPES/NaCl buffer+250 µl defibrinated plasma (point 1);
  for the APC: 250 µl HEPES/NaCl buffer+250 µl defibrinated plasma+125 µl APC;
  for the plasma sample: 125 µl HEPES/NaCl buffer+125 µl defibrinated plasma+125 µl APC+125 µl defibrinated plasma sample of the plasma that is to be analyzed for activated factors.

50 µl citrate buffer, 140 µl HEPES/NaCl buffer and 10 µl phospholipid suspension, made according to point 4, is added to each formulation and incubated for 5 minutes at 37° C. The reaction is started with 10 µl CaCl$_2$ solution, after 5 minutes and 10 minutes, 50 µl of the mixture is added each time to 50 µl of a predefined EDTA solution (EDTA= ethylene diamine tetraacidic acid) to stop the thrombin generation.

6. Test For Thrombin Activity

The method is basically know and is supplied as a set. It is only mentioned for the sake of completeness.

Required Reagents:

Chromogenic substrate S 2238, Chromogenix. item no. 41202. The content of one bottle of S 2238 (25 mg) is dissolved in 20 ml of distilled water; a working dilution of 1 mM is produced by diluting with distilled water at a ratio of 1:1. Thrombin, 53 nkat, Chromogenix, item no. 41217, is dissolved in 1 ml distilled water. A buffer concentrate of 500 mM Tris, 75 mM EDTA, 10% G/V PEG 6000, pH 8.4, is diluted with distilled water 1:10. A working buffer is made by mixing buffer concentrate (30 ml) with human serum albumin (HSA), 20% HSA (0.75 ml). From this, a substrate buffer is mixed, containing 26 ml working buffer and 2.4 ml substrate solution.

20 µl of the sample amounts, called "pipetting scheme" under point 5.1, are each mixed with 500 µl substrate buffer that has been preheated to 37° C. The extinction is measured at one-minute intervals. To control the linearity of substrate splitting, 5 extinction cycles of 1 minute each are measured at 405 nm. A calibration line is established by diluting thrombin with working buffer in the range of 5.3 to 0.53 nkat.

The following results were achieved with virus-inactivated plasma samples, as produced in point 5:

1,2,3 . . . different production batches of virus-inactivated plasma

| B* | APC | 1 | 2 | 3 | 4 |
|---|---|---|---|---|---|
| 0.003 | 0.028 | 0.036 | 0.035 | 0.035 | 0.033 |
| 5 | 6 | 7 | 8 | 9 | 10 |
| 0.041 | 0.038 | 0.057 | 0.045 | 0.060 | 0.051 |

B* blind value

The numbers presented are extinction changes per minute and have been obtained after an incubation of 10 minutes at the thrombin generation test. The measurement at 5 minutes incubation time provides no or very small extinction changes.

To evaluate for thrombin generation from activated clotting factors, the values for APC and the blind value are subtracted from the measured extinction difference per minute. In the example of batch 9, this results in a value of 0.029. At a calibration line with thrombin dilution, a thrombin activity reading of 2 nkat is obtained.

If plasma samples contain heparin, the heparin must be neutralized prior to the test with protamine sulfate or Polybren™ (hexadimethrine bromide) or preferably inactivated with heparinase.

Example 2—Detection of Activated Factor IX, Factor XI and Factor XII:

Factor IXa, factor XIa and factor XIIa have been obtained from Alexis, items no. 73510-1, 200-039-C025 and 200-042-UC02. Defibrinated plasma has been activated through incubation with Thrombin (1.66 nkat, 10 min at 37° C.), thereafter, the thrombin activity was inhibited with Pefabloc SC™ (4-(2-aminoethyl)-benzo sulphonyl fluoride hydrochloride), Boehringer Mannheim, item no. 1 429 868. The amount of Pefabloc SC™ required to inhibit the thrombin activity at hand has been determined in a pretest.

Pipetting Scheme:
  blind value: 250 µl HEPES/NaCl buffer+250 µl defibrinated plasma;
  APC: 125 µl APC+125 µl HEPES/NaCl buffer+250 µl defibrinated plasma;
  factor IXa, 10 µl of a solution with 0.2 plasma units or 10 µl factor XIa or 10 µl factor XIIa+125 µl APC+115 µl HEPES/NaCl buffer+250 µl defibrinated plasma.

Thereafter, 50µl citrate buffer, 140 µl HEPES/NaCl buffer and 10 µl phospholipid suspension, made according to example 1, point 4, is added to each formulation and incubated for 5 minutes at 37 °0C. The reaction is started with 10 µl CaCl$_2$ solution, after 5 minutes and 10 minutes, 50 µl of the mixture is added each time to 50 µl of a predefined EDTA solution to stop the thrombin generation.

| B* | APC | F IXa + APC | F XIa + APC | F XIIa + APC | Incubation time in thrombin generation test |
|---|---|---|---|---|---|
| 0.003 | 0.006 | 0.130 | 0.034 | 0.052 | 5 min |
| 0.022 | 0.039 | 0.122 | 0.083 | 0.088 | 10 min |

*blind value

The manufacturer of factor IXa, factor XIa and factor XIIa only lists the activity in plasma units for factor IXa, where one plasma unit corresponds to the amount of the factor in 1 ml standard plasma. Using the pipetting scheme and the test process, one can calculate that in the test 0.003 plasma units factor IXa initiate a clearly measurable thrombin generation after an incubation time of only 5 minutes.

Example 3—Detection of Activated Factor VII:

Factor VIIa has been obtained from Alexis, item no. 73560-1 or HF086-1. Defibrinated plasma was not activated with thrombin. Pipetting scheme and test procedure were the same as stated in example 2. In the thrombin generation test with factor VIIa, phospholipid vesicles with and without integrated tissue factor as cofactor were analyzed in direct comparison. Vesicles without tissue were used in undiluted form, while vesicles with integrated tissue factor had to be pre-diluted by a factor of 2000. The following results were obtained in such a comparison:

| | B* | APC | F VIIa + APC | incubation time in the thrombin generation test |
|---|---|---|---|---|
| vesicles without tissue factor | 0.003 | 0.026 | 0.035 | 10 min |
| vesicles with tissue factor | 0.015 | 0.039 | 0.061 | 10 min |

*blind value

With both test series, there were 0.002 plasma units factor VIIa in the test. In a test series with vesicles with integrated tissue factor, 0.001 plasma units factor VIIa were still clearly detectable.

There has thus been shown and described a novel method to determine activated blood clotting factors in plasma and plasma derivatives which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A method for determining activated clotting factors in plasma and plasma derivatives, using the following processing steps:

a) incubating a sample amount of plasma or plasma derivative with activated prothrombin complex and procoagulating phospholipid vesicles, the latter containing integrated tissue factor, and the thrombin generation is initiated by adding a suitable amount of $Ca^{2+}$ ions, b) after a specified incubation time of 5 min and 10 min, the thrombin generation is ended and the amount of generated thrombin is measured using known methods.

2. The method set forth in claim 1, wherein the content of factor Xa in the activated prothrombin complex is about 1% of the total factor X content with a non-measurable content of factor IIa.

3. The method set forth in claim 1, wherein the tissue factor is produced from biogenic starting material.

4. The method set forth in claim 3, wherein the tissue factor is extracted from bovine brain with a detergent-containing solution of dry acetone powder.

5. The method set forth in claim 1, wherein the tissue factor is integrated in procoagulating phospholipid vesicles.

6. The method set forth in claim 4, wherein the tissue factor is mixed in a detergent-containing solution with phosphatidylserine and phosphatidylcholine and integrated in the procoagulating phospholipid vesicles by dialysis.

7. The method set forth in claim 5, wherein the tissue factor is mixed in a detergent-containing solution with phosphatidylserine and phosphatidylcholine and integrated in the procoagulating phospholipid vesicles by dialysis.

* * * * *